United States Patent [19]

Kawaguchi

[11] Patent Number: 4,936,773
[45] Date of Patent: Jun. 26, 1990

[54] ORTHODONTIC APPARATUS HAVING AN IMPROVED BASE PORTION

[75] Inventor: Kozo Kawaguchi, Fukushima, Japan

[73] Assignee: GAC International, Inc., Central Islip, N.Y.

[21] Appl. No.: 305,801

[22] Filed: Feb. 2, 1989

[51] Int. Cl.⁵ .............................................. A61C 3/00
[52] U.S. Cl. ............................................ 433/9; 433/8
[58] Field of Search ............................... 433/8, 9

[56] References Cited

U.S. PATENT DOCUMENTS

| | | | |
|---|---|---|---|
| 4,068,379 | 1/1978 | Miller et al. | 433/9 |
| 4,219,617 | 8/1980 | Wallshein | 433/8 |
| 4,243,386 | 1/1981 | Kawaguichi | 433/9 |
| 4,310,306 | 1/1982 | Wallshein | 433/9 |
| 4,322,206 | 3/1982 | Reynolds | 433/9 |
| 4,415,330 | 11/1983 | Daisley et al. | 433/8 |
| 4,604,057 | 8/1986 | Viglietti | 433/9 |
| 4,639,218 | 1/1987 | Jones et al. | 433/8 |
| 4,659,309 | 4/1987 | Merkel | 433/9 |
| 4,681,538 | 7/1987 | DeLuca et al. | 433/9 |
| 4,826,430 | 5/1989 | Chen et al. | 433/9 |

Primary Examiner—John J. Wilson
Attorney, Agent, or Firm—Kenyon & Kenyon

[57] ABSTRACT

A ceramic orthodontic apparatus for attachment to a tooth has a base portion with a tooth abutting surface. The tooth abutting surface is shaped to fit generally the morphology of a tooth and defines a plurality of spaced, radially contoured indentations for receiving adhesive material for attaching the apparatus to a tooth.

38 Claims, 2 Drawing Sheets

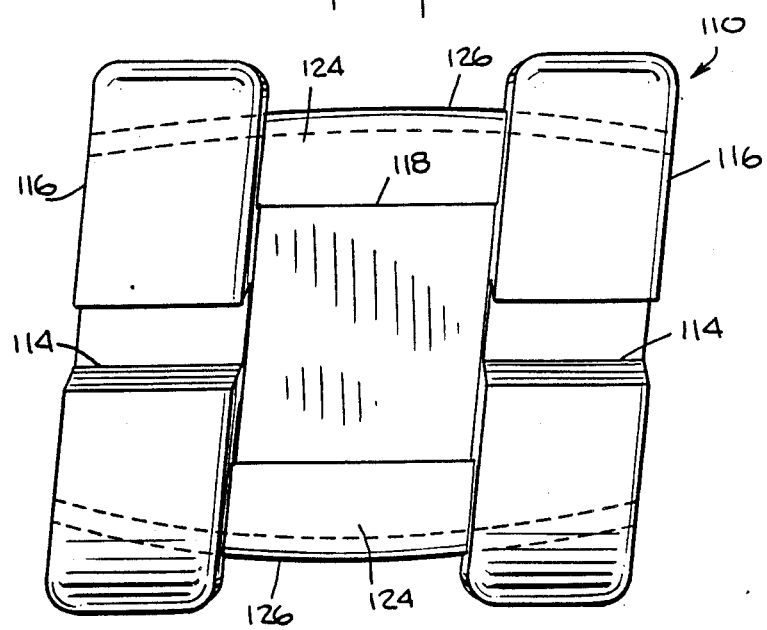
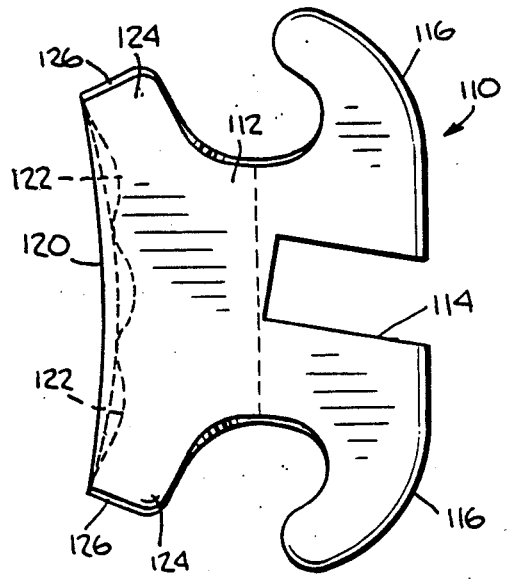
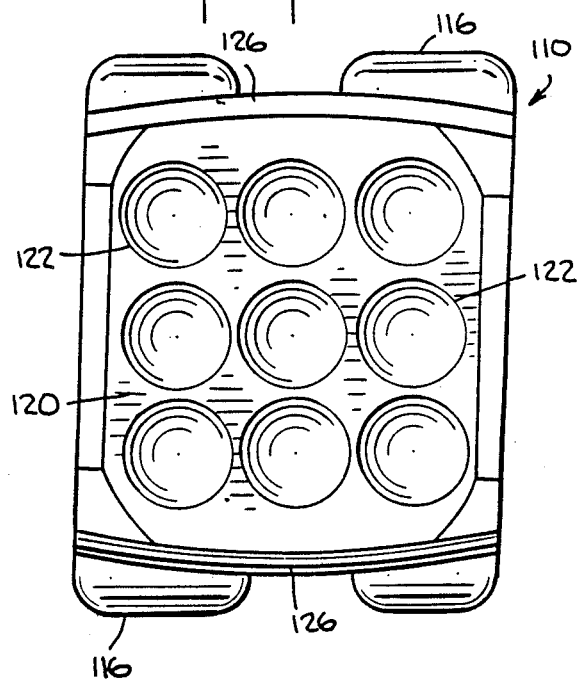

ORTHODONTIC APPARATUS HAVING AN IMPROVED BASE PORTION

BACKGROUND OF THE INVENTION

1. Field of the Invention

The invention is directed to orthodontic apparatus, and, more particularly, to ceramic orthodontic apparatus having base portions for directly attaching the apparatus to the surface of a tooth.

2. Background Information

Known orthodontic brackets typically comprise a base portion, which defines an archwire slot for receiving an archwire, and tie wings projecting outwardly from the base portion for attaching ligature wire to secure the archwire to the bracket. The base portion further defines a tooth abutting surface shaped generally to conform to the morphology of a tooth. The bracket is mounted to a tooth by applying cement to the tooth abutting surface and then positioning and pressing the bracket against the surface of the tooth. It is desirable to bond the bracket to the tooth with adequate strength to withstand the ordinary forces exerted by the musculature and orthodontic appliances connected to the bracket. However, if the bond strength between the bracket and the tooth is too strong it may be difficult to remove the bracket after treatment without damaging the enamel surface of the tooth.

Most known ceramic brackets have a smooth tooth abutting surface. Such brackets are generally mounted to a tooth by first applying a silane compound to the tooth abutting surface and then applying cement to the silane coated surface. The silane compound improves the strength of the bond between the bracket and the tooth. One problem associated with such brackets is that the debonding procedure is often time consuming and painful to the patient. Because of the strength of the silane bond and brittle nature of the ceramic bracket, such brackets often fracture upon removal leaving pieces of both ceramic and cement bonded to the tooth. These pieces must be removed with diamond burrs, which can be a time-consuming, painful procedure, that frequently damages the enamel surface of the tooth.

One type of known ceramic bracket has relatively deep rectangular, or square shaped pockets with sharp corners formed in the tooth abutting surface for receiving cement. The deep pockets are provided to increase the bonding surface area, and thus increase the strength of the bond between the bracket and the tooth. The shape and depth of the pockets, however, makes it difficult to intimately apply cement to the pocket surfaces. As a result, after the cement sets air gaps form between the cement and the surfaces of the pockets. Accordingly, the strength of the bond between the tooth and bracket decreases, and may cause the bond to fail under normal loading forces.

Another type of known ceramic bracket has one or more V-shaped grooves formed on the tooth abutting surface for receiving cement. The V-shaped groove is provided to improve the bond between the bracket and the tooth. However, one problem associated with both brackets having a V-shaped groove and brackets having rectangular or square shaped pockets, is that the sharp corners of the grooves or pockets are points of concentrated stress. This problem is especially critical in the region of the base of the archwire slot where the cross sectional area of the bracket is thinnest. The concentrated stress can cause the bracket to fracture between the bottom of the V-shaped groove or pocket and the base of the archwire slot when normally experienced forces are exerted on the bracket.

Another problem with known ceramic brackets occurs when the brackets are mounted to a tooth. When the brackets are pressed against a tooth excess cement is squeezed from underneath the bracket and against the base portion beneath the tie wings. This condition must be checked, and the cement must be removed several times while mounting the bracket to a tooth. If the cement is not removed, it will set in the space beneath the tie wing and prevent the ligature wire from fitting around the tie wing to secure the archwire to the bracket.

This problem has been solved with some metal brackets by extending a flange or base member outwardly from the tooth abutting surface of the base portion and beneath the tie wings. The flange prevents any cement from collecting beneath the tie wings and leaves sufficient space below the tie wings to wrap the ligature wire around the bracket. Ceramic brackets with V-shaped grooves or square pockets, however, cannot avoid this problem by extending a flange from the base portion beneath the tie wings. The flange must be thicker than at least the depth of the cement pockets or grooves in order for the bracket to have sufficient structural strength to withstand normal loading forces. Therefore, in order to provide a flange of sufficient thickness and maintain sufficient spacing between the flange and the tie wings for wrapping the ligature wire, the overall vertical height of the bracket must be increased. This condition is uncomfortable for patients. As a result, known ceramic brackets are generally not provided with a flange beneath the tie wings, and accordingly, such brackets require removal of excess cement from around the base portion of a bracket while mounting the bracket to a tooth.

Yet another disadvantage associated with known ceramic brackets is the problem of debonding the bracket from a tooth without fracturing the enamel surface of the tooth. Some known metal orthodontic brackets can be mounted to a tooth by applying adhesive to a screen mesh base. When debonding, the malleability of the mesh base permits the bracket, in effect, to be peeled from the surface of the tooth. As a result, such brackets are generally removable from a tooth without damaging the enamel surface of the tooth. Ceramic brackets, on the other hand, are rigid and brittle in comparison to the mesh base of a metal bracket. As a result, known ceramic brackets often fracture upon removal. If the strength of the adhesive bonds between the bracket and cement, and between the bracket and the surface of the tooth, are stronger than the enamel surface of the tooth itself, removal of the ceramic bracket may fracture the enamel surface of the tooth.

The orthodontic apparatus of the invention overcomes the problems and disadvantages of known orthodontic apparatus and provides an improved base portion for directly bonding the apparatus to the surface of a tooth.

SUMMARY OF THE INVENTION

The invention is directed to a ceramic orthodontic apparatus having a base portion for attaching the apparatus directly to the surface of a tooth. The base portion has a tooth abutting surface shaped to fit generally the morphology of a tooth and defining a plurality of spaced, radially contoured indentations for receiving adhesive material for attaching the apparatus to a tooth.

Another apparatus of the invention is directed to a ceramic orthodontic bracket for attachment to a tooth comprising a base portion defining an archwire slot for receiving an archwire. The base portion of the bracket further defines a tooth abutting surface defining a plurality of spaced, radially contoured indentations for receiving adhesive material for directly attaching the bracket to a tooth.

The orthodontic bracket of the invention preferably includes two flange portions extending outwardly from opposite sides of the base portion and extending along a bottom edge of the base portion in the axial direction of the archwire slot. Each flange portion of the bracket preferably defines an outer face extending in the axial direction of the archwire slot that slopes inwardly toward the tooth abutting surface for retaining excess adhesive material beneath or against the respective flange portion. The peripheral contour of each flange portion is preferably curved so that the width of the base portion is narrower toward the ends of the bracket in the axial direction of the archwire slot to facilitate the attachment of ligature or elastomeric products to the bracket.

Another apparatus of the invention is directed to a ceramic orthodontic apparatus having a base portion for attaching the apparatus to a tooth. The base portion defines a tooth abutting surface shaped to fit the morphology of a tooth. The tooth abutting surface defines a plurality of raised portions and adjacent lowered portions, and the lowered portions define spaced, radially contoured indentations in the tooth abutting surface. The transition areas between the raised and lowered portions of the tooth abutting surface are rounded for receiving adhesive material for attaching the apparatus to a tooth.

One advantage of the apparatus of the invention is that the radial contour of the indentations in the tooth abutting surface permits cement to be easily applied in intimate contact with the surfaces thereof, and thus increases the bonding strength between the cement and the bracket over known apparatus. Another advantage of the apparatus of the invention is that the radial contours of the indentations of the tooth abutting surface do not give rise to points of concentrated stress within the bracket as experienced with known brackets having V-shaped grooves, rectangular, square, or other types of sharp cornered indentations. The structure of the base portion of the invention has also proven to permit the apparatus to be more easily debonded from a tooth without fracturing the apparatus or the enamel surface of the tooth.

Other advantages of the orthodontic apparatus of the invention will become apparent in view of the following detailed description and drawings taken in connection therewith.

BRIEF DESCRIPTION OF THE DRAWINGS

FIG. 4 is a top planar view of another orthodontic apparatus of the invention having a generally rhomboidal configuration.

FIG. 5 is a side planar view of the apparatus of FIG. 4.

FIG. 6 is a bottom planar view of the apparatus of FIG. 4 illustrating an improved base portion of the invention for directly bonding the apparatus to a tooth.

DETAILED DESCRIPTION OF PREFERRED EMBODIMENTS

Figure 1:
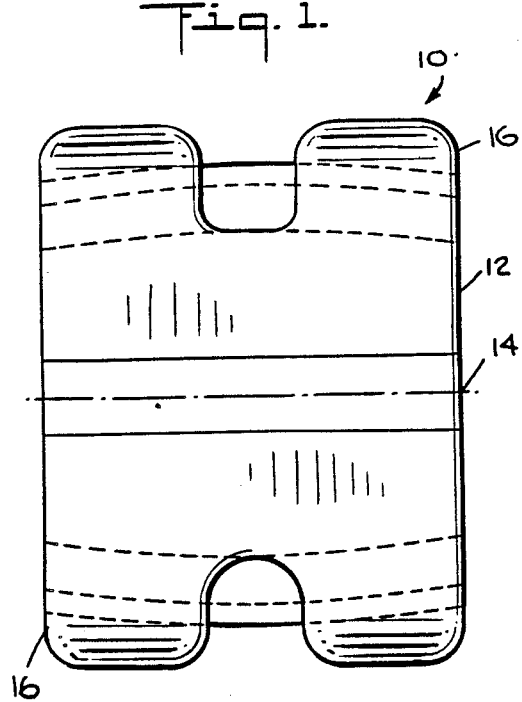
FIG. 1 is a top planar view of an orthodontic apparatus embodying the invention including a base portion for directly attaching the apparatus to a tooth.
Figure 2:
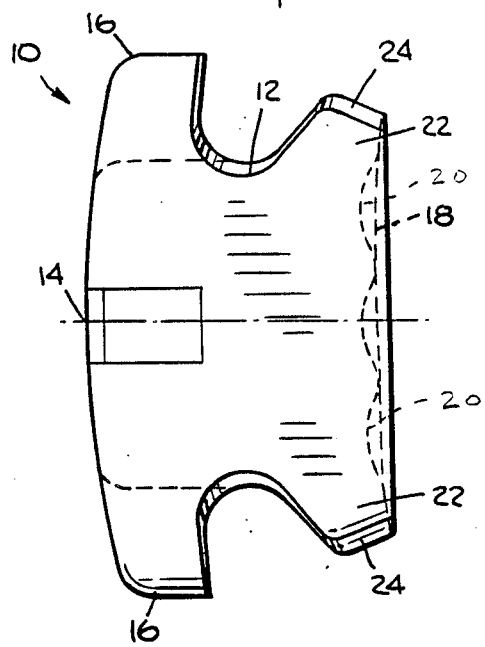
FIG. 2 is a side planar view of the apparatus of FIG. 1.

In FIG. 1 an orthodontic bracket embodying the invention is illustrated as 10. The orthodontic bracket 10 comprises a base portion 12 defining an archwire slot 14 therein for receiving an archwire, not shown. The bracket 10 further includes tie wing portions 16, 16 extending outwardly therefrom for tying ligature wire, not shown, for securing an archwire to the bracket. The base portion 12 of the bracket further defines a tooth abutting surface 18, which, as can be seen in FIG. 2, is shaped to fit generally the morphology of a tooth. The bracket 10 is made of a ceramic material, such as a single crystal or polycrystalline aluminum oxide.

Figure 3:
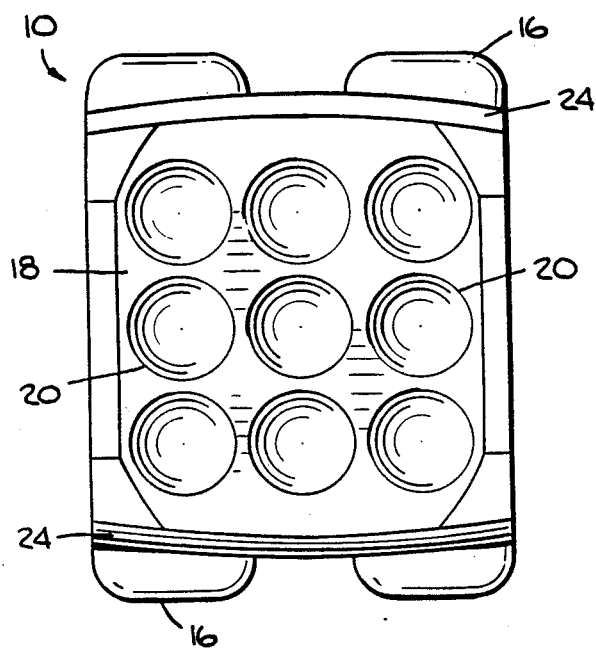
FIG. 3 is a bottom planar view of the apparatus of FIG. 1 illustrating an improved base portion of the invention for directly bonding the apparatus to a tooth.

Turning to FIG. 3, the tooth abutting surface 18 defines a plurality of radially contoured indentations 20, 20 therein, for receiving adhesive material, not shown, for directly attaching the bracket 10 to the surface of a tooth. The indentations 20, 20 are preferably arranged in several parallel rows, as shown in FIG. 3. Although the indentations 20, 20 each define a circular shaped periphery in the tooth abutting surface 18, they may be formed with a different shaped periphery, such as an oval. Likewise the indentations 20, 20 do not have to be formed in rows, as shown in FIG. 3, but may be staggered or arranged in another type of pattern.

The orthodontic bracket 10 further includes flange portions 22, 22 extending outwardly from the base portion 12. The flange portions 22, 22 define outer surfaces 24, 24 extending along the base portion of the bracket 10. The outer surfaces 24, 24 slope inwardly toward the tooth abutting surface 18. As shown in FIG. 3, the contour of the surfaces 24, 24 are curved so that the width of the base 12 becomes narrower toward the ends of the bracket 10 in the axial direction of the archwire slot 14. When the bracket 10 is mounted to a tooth, adhesive material squeezed toward the periphery of the base portion from the indentations 20, 20 is either retained beneath the flange portions 22, 22 or beneath the sloped surfaces 24, 24, as hereinafter described in further detail.

To mount the bracket 10 to a tooth, a silane compound, known in the art, is preferably applied to the surface 18. Adhesive material is then applied to the silane coated surface 18 and pressed into the indentations 20, 20. The silane coated surface improves the strength of the bond between the adhesive and the bracket. The radial contours of the indentations permit adhesive material to be applied in intimate contact thereto without forming air pockets that decrease the bond strength between the adhesive material and the bracket, as with known brackets having sharp cornered indentations.

The bracket is attached to a tooth, not shown, by pressing the tooth abutting surface 18 against the surface of the tooth and positioning the bracket as required. Any excess adhesive material that flows toward the outer periphery of the base portion is retained either between the surface 18 and the tooth surface, or against the sloped surfaces 24, 24. Unlike known ceramic brackets, it is not necessary to remove adhesive material from the edges of the bracket during mounting in order to leave sufficient space to wrap ligature wire around the tie wings. The flange portions 22, 22 ensure that sufficient space is retained beneath the tie wings to fit the ligature wire, regardless of the quantity of adhesive material that flows from underneath the bracket. The curved contours of the surfaces 24, 24 permit ligature wire or elastomeric products to be easily attached to the bracket 10. The ligature is first placed around the narrow ends of the bracket, which, because of their curved contours, are easily accessible, and the ligature is then worked around the remainder of the bracket's edge.

As shown in FIG. 2, the indentations 20, 20 are not very deep in relation to the overall vertical height of the bracket 10. As a result, the bracket 10 can be formed with the flange portions 22, 22 to ensure that the space underneath the tie wings 16, 16 remains free of excess cement, without noticeably increasing the overall vertical height of the bracket. Known brackets with deeper pockets, on the other hand, require a thicker flange member to provide adequate structural strength in those areas of the flange closest to the pockets. The overall vertical height of a known bracket, therefore, would substantially increase and cause discomfort to a patient.

Turning to FIGS. 4 through 6, another ceramic orthodontic bracket embodying the invention is illustrated as 110. As can be seen, the bracket 110 has a generally rhomboidal configuration which facilitates the process of aligning the bracket 110 on a tooth. The bracket 110 comprises a base portion 112 defining an archwire slot 114 for receiving an archwire, not shown. The bracket 110 further includes a pair of split tie wing portions 116, 116 defining a channel 118 therebetween. As best shown in FIG. 5, the archwire slot 114 is inclined in relation to the vertical axis of the bracket 110. The base portion 112 of the bracket 110 defines a tooth abutting surface 120 which, as can be seen, is shaped to fit the morphology of a tooth.

The tooth abutting surface 120 defines a plurality of radially contoured indentations 122, 122 therein, for receiving adhesive material, not shown, for directly attaching the bracket 110 to the surface of a tooth. The bracket 110 further includes a pair of flange portions 124, 124 defining outer surfaces 126, 126 extending along the length of the base portion 112 in the axial direction of the archwire slot 114. The outer surfaces 126, 126 slope inwardly toward the tooth abutting surface 120. The shape and configuration of the tooth abutting surface 120, the indentations 122, 122, and flange portions 124, 124 are substantially the same as the corresponding elements described above in relation to the previous embodiment. As shown, the contour of the surfaces 126, 126 are curved so that the width of the base 112 is narrower toward the ends of the bracket 110 in the axial direction of slot 114 in order to facilitate the attachment of ligature or elastomeric products, as described above in relation to the surfaces 24, 24 of the previous embodiment.

As described above in relation to the previous embodiment, the bracket 110 is also preferably mounted to a tooth by first applying a silane compound to the surface 120, and then applying adhesive material to the silane coated surface to attach the bracket to the tooth. It should be noted that ceramic brackets embodying the invention have proven to provide sufficient bonding strength between the bracket and the tooth to withstand normal loading forces. However, brackets embodying the invention have also proven to be more easily debonded from tooth surfaces than known ceramic brackets without fracturing the bracket or damaging the enamel surface of the tooth. The bracket is preferably removed from a tooth by gripping either side of the bracket with orthodontic pliers and applying a rotational, peel movement to break the bond between the bracket and the tooth.

In the foregoing specification, the invention has been described with reference to particular exemplary embodiments thereof. However, it will be evident that various modifications and changes may be made thereto without departing from the scope of the appended claims. The specification and drawings are, accordingly, to be regarded in an illustrative rather than in a restrictive sense.

What is claimed is:

1. A ceramic orthodontic apparatus having a base portion for attaching said apparatus to a tooth, wherein
    said base portion defines a tooth abutting surface shaped to fit generally the morphology of a tooth, said tooth abutting surface defining a plurality of spaced, radially contoured indentations therein for receiving adhesive material for attaching said apparatus to a tooth, each of said indentations defining a wide, shallow profile, said profile being defined by at least one radius of curvature centered over the tooth side of said tooth abutting surface, said indentations being closely spaced to one another so as to leave narrow transitional areas therebetween in comparison to the width of each of said indentations.

2. A ceramic orthodontic apparatus as defined in claim 1, said apparatus further comprising:
    at least one tie wing extending outwardly from said base portion; and
    said base portion further defines an archwire slot in a surface thereof to receive an archwire.

3. A ceramic orthodontic apparatus as defined in claim 2, said apparatus further comprising:
    a flange portion extending outwardly from said base portion along the bottom edge thereof, said flange portion extending substantially in the axial direction of said archwire slot beneath said tie wing, said flange portion preventing excess adhesive material from collecting beneath said tie wing.

4. A ceramic orthodontic apparatus as defined in claim 3, wherein
    each of said indentations defines a circular shaped edge in said tooth abutting surface, the contours of each of said indentations being defined substantially by one radius of curvature.

5. A ceramic orthodontic apparatus as defined in claim 4, wherein
    said flange portion defines an outside face extending substantially in the axial direction of said archwire slot, said face being sloped inwardly toward said tooth abutting surface.

6. A ceramic orthodontic apparatus as defined in claim 5, wherein
    said apparatus comprises two of said flange portions, each of said flange portions being located on an opposite side of said base portion.

7. A ceramic orthodontic apparatus as defined in claim 6, wherein
    the outside face of each of said flange portions is curved inwardly toward either end thereof to facilitate attaching ligature or elastomeric products to said apparatus.

8. A ceramic orthodontic apparatus as defined in claim 7, wherein
said apparatus comprises an aluminum oxide ceramic material.

9. A ceramic orthodontic apparatus as defined in claim 1, wherein
said radially contoured indentations are arranged in substantially parallel rows.

10. A ceramic orthodontic apparatus as defined in claim 9, wherein
said apparatus defines approximately three rows of said indentations, each of said rows including approximately three of said indentations.

11. A ceramic orthodontic apparatus as defined in claim 1, wherein
said tooth abutting surfaces and said indentations define substantially smooth surfaces.

12. A ceramic orthodontic bracket for attachment to a tooth, said bracket comprising:
a base portion defining an archwire slot therein to receive an archwire, said base portion further defining a tooth abutting surface, said tooth abutting surface defining a plurality of spaced, radially contoured indentations therein for receiving adhesive material for attaching said bracket to a tooth, said indentations each being defined by a wide, low contour, the contour of each of said indentations being defined by at least one radius of curvature centered away from said tooth abutting surface, said indentations being closely spaced to each other so as to form narrow transitional areas therebetween relative to the widths of said indentations.

13. An orthodontic bracket as defined in claim 12, said bracket further comprising:
at least two flange portions, said flange portions extending outwardly from opposite sides of said base portion and each extending along a bottom edge thereof in substantially the axial direction of said archwire slot.

14. An orthodontic bracket as defined in claim 13, wherein
an edge of each of said flange portions is curved so that the width of said base portion is narrower toward the ends of said bracket in the axial direction of said archwire slot to facilitate the attachment of ligature or elastomeric products to said bracket.

15. An orthodontic bracket as defined in claim 12, wherein
each of said radially contoured indentations defines a circular shaped periphery in said tooth abutting surface, the contour of each of said indentations being defined substantially by one radius of curvature.

16. An orthodontic bracket as defined in claim 12, wherein
said bracket is made of an aluminum oxide ceramic material.

17. An orthodontic bracket as defined in claim 12, wherein
the opposite edges of said bracket extending in the axial direction of said archwire slot are substantially parallel and the other opposite edges of said bracket are substantially parallel, so that the planes of said edges extending in the axial direction of said archwire slot intersect the planes of said other edges so that said bracket edges form of substantially rhomboidal configuration.

18. An orthodontic bracket as defined in claim 12, wherein
said tooth abutting surface is coated with a silane compound for improving the bond between said bracket and a tooth.

19. An orthodontic bracket as defined in claim 12, wherein
said indentations are arranged in substantially parallel rows.

20. An orthodontic bracket as defined in claim 19, wherein
said bracket defines approximately three of said rows with approximately three of said indentations in each of said rows.

21. A ceramic orthodontic apparatus comprising:
a base portion defining a tooth abutting surface shaped to fit generally the morphology of a tooth, said tooth abutting surface defining a plurality of raised portions and adjacent lowered portions, each of said lowered portions defining a radially contoured indentation in said tooth abutting surface, each of said indentations defining a wide, shallow radial contour, said radial contour being defined by at least one radius of curvature centered above said tooth abutting surface, said indentations being closely spaced to each other so as to form narrow transitional areas therebetween in comparison to the width of each of said indentations, said transitional areas between said raised and lowered portions being rounded for receiving adhesive material for attaching said apparatus to a tooth.

22. A ceramic orthodontic apparatus as defined in claim 21, said apparatus further comprising:
at least one tie wing projecting outwardly from said base portion; and
said base portion further defines an archwire slot therein to receive an archwire.

23. A ceramic orthodontic apparatus as defined in claim 22, said apparatus further comprising:
at least one flange portion projecting outwardly from said base portion along a bottom edge thereof and extending substantially in the axial direction of said archwire slot.

24. A ceramic orthodontic apparatus as defined in claim 23, wherein
said at least one flange portion defines an outer face, said outer face extending substantially in the axial direction of said archwire slot and being sloped inwardly toward said tooth abutting surface.

25. A ceramic orthodontic apparatus as defined in claim 24, wherein
each of said lowered portions defines a circular shaped edge in said tooth abutting surface, the contour of each of said lowered portions being defined substantially by a single radius of curvature.

26. A ceramic orthodontic apparatus as defined in claim 25, wherein
said apparatus comprises two of said flange portions, each of said flange portions extending along an opposite side of said base portion.

27. A ceramic orthodontic apparatus as defined in claim 26, wherein
said outer face of each of said flange portions is curved inwardly toward either end thereof to facilitate attaching ligature or elastomeric products to said apparatus.

28. A ceramic orthodontic apparatus as defined in claim 27, wherein
the opposite sides of said base portion extending substantially in the axial direction of said archwire slot are substantially parallel, and the other opposite sides of said base portion are substantially parallel, the planes of said sides extending substantially in the axial direction of said archwire slot intersecting the planes of said other sides to form a substantially rhomboidal configuration.

29. A ceramic orthodontic apparatus as defined in claim 21, wherein
said lowered portions defining said radially contoured indentations are arranged in substantially parallel rows.

30. A ceramic orthodontic apparatus as defined in claim 29, wherein
said apparatus includes about three of said rows with about three of said lowered portions in each of said rows.

31. A ceramic orthodontic bracket for attachment to a tooth, said bracket comprising:
a base portion defining an archwire slot therein to receive an archwire, said base portion further defining a tooth abutting surface, said tooth abutting surface defining a plurality of spaced, radially contoured indentations therein to receive adhesive material to attach said bracket to a tooth; and
at least two flange portions, each of said flange portions extending outwardly from opposite sides of said base portion and extending along a bottom edge of said base portion in the axial direction of said archwire slot, the outer face of each of said flange portions extending in the axial direction of said archwire slot being inclined inwardly toward said tooth abutting surface to retain excess adhesive material beneath or against said flange portions.

32. A ceramic orthodontic bracket as defined in claim 31, said bracket further comprising:
at least one tie wing extending outwardly from said base portion, wherein one of said flange portions is located beneath said tie wing to prevent adhesive material from collecting beneath said tie wing.

33. A ceramic orthodontic apparatus as defined in claim 32, wherein
the outside face of each of said flange portions is curved inwardly toward either end thereof to facilitate attaching ligature or elastomeric products to said apparatus.

34. A ceramic orthodontic apparatus as defined in claim 33, wherein
said apparatus includes an aluminum oxide ceramic material.

35. A ceramic orthodontic apparatus as defined in claim 31, wherein
each of said radially contoured indentations is defined by a relatively wide, low contour, the contour of each of said indentation being defined by at least one radius of curvature centered over the tooth side of said tooth abutting surface, said indentations being closely spaced relative to each other so as to leave narrow transitional areas therebetween.

36. A ceramic orthodontic apparatus as defined in claim 35, wherein
said indentations are arranged in substantially parallel rows.

37. A ceramic orthodontic apparatus as defined in claim 36, wherein
said apparatus includes about three of said rows, with about three of said indentations in each of said rows.

38. A ceramic orthodontic appliance, said appliance comprising:
a base portion and a tie wing projecting outwardly from said base portion, said base portion defining a slot arranged to receive an archwire and a tooth abutting surface shaped to substantially correspond to the morphology of a tooth, said tooth abutting surface defining a plurality of radially contoured indentations therein for receiving adhesive material to mount said appliance to a tooth, each of said indentations defining a wide, shallow profile, said profile being defined by at least one radius of curvature centered over said tooth abutting surface, said indentations being arranged in about three substantially parallel rows, each of the rows including about three of said indentations.

* * * * *

UNITED STATES PATENT AND TRADEMARK OFFICE
CERTIFICATE OF CORRECTION

PATENT NO. : 4,936,773
DATED : June 26, 1990
INVENTOR(S) : Kozo KAWAGUCHI

It is certified that error appears in the above-identified patent and that said Letters Patent is hereby corrected as shown below:

Column 10, line 15, change "indentation" to --indentations--.

Signed and Sealed this

Nineteenth Day of November, 1991

Attest:

HARRY F. MANBECK, JR.

*Attesting Officer*     *Commissioner of Patents and Trademarks*